US012734130B2

(12) United States Patent
Kipping et al.

(10) Patent No.: US 12,734,130 B2
(45) Date of Patent: Sep. 15, 2026

(54) PHARMACEUTICAL COMPOSITION AND METHOD FOR ENHANCING SOLUBILITY OF POORLY SOLUBLE ACTIVE PHARMACEUTICAL INGREDIENTS

(71) Applicant: Merck Patent GmbH, Darmstadt (DE)

(72) Inventors: Thomas Kipping, Darmstadt (DE); Finn Bauer, Darmstadt (DE); Nicole Di Gallo, Darmstadt (DE); Anja-Nadine Knuettel, Darmstadt (DE); Alessandro Giuseppe Elia, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 440 days.

(21) Appl. No.: 18/034,260

(22) PCT Filed: Oct. 27, 2021

(86) PCT No.: PCT/EP2021/079787

§ 371 (c)(1),
(2) Date: Apr. 27, 2023

(87) PCT Pub. No.: WO2022/090296

PCT Pub. Date: May 5, 2022

(65) Prior Publication Data

US 2023/0390204 A1 Dec. 7, 2023

(30) Foreign Application Priority Data

Oct. 28, 2020 (EP) .................................... 20204466

(51) Int. Cl.
*A61K 9/16* (2006.01)
*A61K 45/06* (2006.01)

(52) U.S. Cl.
CPC ............ *A61K 9/1635* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2018/0280302 | A1* | 10/2018 | Kucera | A61K 31/496 |
| 2019/0274961 | A1 | 9/2019 | Zheng et al. | |
| 2019/0290590 | A1* | 9/2019 | Zheng | A61P 31/10 |
| 2019/0298655 | A1 | 10/2019 | Zheng et al. | |
| 2020/0146977 | A1 | 5/2020 | Umemoto et al. | |

FOREIGN PATENT DOCUMENTS

| | | | |
|---|---|---|---|
| WO | 2018083286 | A1 | 5/2018 |
| WO | 2018199282 | A1 | 11/2018 |

OTHER PUBLICATIONS

Brough, AAPS PharmSciTech, 17, 1, 2016 (Year: 2016).*
Gift et al., Influence of polymeric excipients on crystal hydrate formation kinetics in aqueous slurries. J Pharm Sci. 2008;97(12):5198-211.
Overhoff et al., Effect of Stabilizer on the Maximum Degree and Extent of Supersaturation and Oral Absorption of Tacrolimus Made By Ultra-Rapid Freezing. Pharmaceutical Research. 2008;25(1):167-75.
De Jaeghere et al., Hot-melt extrusion of polyvinyl alcohol for oral immediate release applications. Int J Pharm. 2015;492(1-2):1-9.
International search report PCT/EP2021/079787 dated Jan. 20, 2022 (pp. 1-2).
Brough Chris et al: "Use of Polyvinyl Alcohol as a Solubility-Enhancing Polymer for Poorly Water Soluble Drug Delivery (Part 1)", AAPS Pharmscitech, Springer US, New York, vol. 17, No. 1, Dec. 4, 2015 (Dec. 4, 2015), pp. 167-179, XP036112594, DOI: 10.1208/S12249-015-0458-Y.

* cited by examiner

*Primary Examiner* — Robert A Wax
*Assistant Examiner* — William Craigo
(74) *Attorney, Agent, or Firm* — Millen, White, Zelano & Branigan P.C.; Ryan R. Pool

(57) ABSTRACT

The present invention relates to pharmaceutical compositions using polymers as an excipient. Particularly, the invention relates to a pharmaceutical composition comprising polyvinyl alcohol which is suitable to enhance solubility of poorly soluble active pharmaceutical ingredients in aqueous media. The present invention also relates to a method for enhancing solubility of poorly soluble active pharmaceutical ingredients.

9 Claims, 4 Drawing Sheets

FIG. 1

| PVA | PVA % by weight | $SiO_2$ % by weight | API | API % by weight | Pressure (Bar) | Melting temp. °C | Torque % of max.Nm [30Nm Brabender/ 12Nm Thermo] | Dosing rate kg/h | Screw speed | Temp. heating zone 1 °C | Temp. heating zone 2 °C | Temp. heating zone 3 °C | Temp. heating zone 4 °C | Temp. heating zone 5 °C |
|---|---|---|---|---|---|---|---|---|---|---|---|---|---|---|
| Poval 5-74 | 88 | 2 | ITZ | 10 | 9 | 214 | 16 | 0,2 | 200 | 80 | 200 | 200 | 200 | 220 |
| Poval 3-80 | 88 | 2 | ITZ | 10 | 9 | 196 | 16 | 0,2 | 200 | 80 | 200 | 200 | 200 | 200 |
| Poval 5-82 | 88 | 2 | ITZ | 10 | 25 | 197 | 15-16 | 0,2 | 200 | 80 | 200 | 200 | 200 | 200 |
| Poval 3-83 | 88 | 2 | ITZ | 10 | 1-3 | 196 | 16-17 | 0,2 | 200 | 80 | 200 | 200 | 200 | 200 |
| Poval 5-88 | 88 | 2 | ITZ | 10 | 12-13 | 196 | 17 | 0,2 | 200 | 80 | 200 | 200 | 200 | 200 |
| Poval 3-88 | 88 | 2 | ITZ | 10 | 9-10 | 196 | 13 | 0,2 | 200 | 80 | 200 | 200 | 200 | 200 |
| Partec MXP | 88 | 2 | ITZ | 10 | 15 | 196 | 18 | 0,2 | 200 | 80 | 200 | 200 | 200 | 200 |
| Poval 4-98 | 88 | 2 | ITZ | 10 | 17 | 225 | 13 | 0,2 | 200 | 80 | 230 | 230 | 230 | 230 |
| Poval 18-88 | 88 | 2 | ITZ | ^10 | 25-26 | 197 | 19-20 | 0,2 | 200 | 80 | 200 | 200 | 200 | 200 |

FIG. 3

| PVA | PVA % by weight | API | API % by weight | Pressure (Bar) | Melting temp. °C | Torque % of max.Nm [30Nm Brabender/ 12Nm Thermo] | Dosing rate kg/h | Screw speed | Temp. heating zone 1 °C | Temp. heating zones 2-7 °C | Temp. heating zone 8 (nozzle) °C |
|---|---|---|---|---|---|---|---|---|---|---|---|
| Poval 3-80 | 90 | Dipyrida mole | 10 | 5-8 | 182 | 37-38 | 0,2 | 200 | 80 | 190 | 200 |
| Poval 3-83 | 90 | Dipyrida mole | 10 | 1-3 | 182 | 35-36 | 0,2 | 200 | 80 | 190 | 190 |
| Parteck MXP | 90 | Dipyrida mole | 10 | 15-20 | 182 | 20 | 0,2 | 200 | 80 | 190 | 190 |
| Parteck MXP | 50 | Dipyrida mole | 50 | 0 | 180 | 15 | 0,15 | 200 | 80 | 190 | 190 |

PHARMACEUTICAL COMPOSITION AND METHOD FOR ENHANCING SOLUBILITY OF POORLY SOLUBLE ACTIVE PHARMACEUTICAL INGREDIENTS

TECHNICAL FIELD

The present invention relates to pharmaceutical compositions using polymers as an excipient. Particularly, the invention relates to a pharmaceutical composition comprising polyvinyl alcohol which is suitable to enhance solubility of poorly soluble active pharmaceutical ingredients in aqueous media. The present invention also relates to a method for enhancing solubility of poorly soluble active pharmaceutical ingredients.

STATE OF THE ART

The use of hydrophilic polymers such as polyvinyl alcohol (PVA) in an excipient for pharmaceutical compositions has been widely described. WO 2018/083285 A1 discloses powdered PVA having improved properties as a polymer matrix in pharmaceutical compositions comprising active ingredients, especially in compressed tablets forming amorphous solid dispersions with poorly soluble active pharmaceutical ingredients (APIs).

The formulation of amorphous solid dispersions is a well-known strategy to improve the bioavailability of poorly water-soluble drug substances. Although the amorphous form exhibits higher solubility, it is rather unstable and tends to re-crystallize and precipitate immediately after dissolution or during the pH change while changing from the acidic gastric environment to the more neutral intestine. The re-crystallized fraction of the API cannot be absorbed. Since drug absorption occurs primarily in the intestines, pharmaceutical formulations that do not sustain high concentration of the APIs in an intestinal solution typically yield only minor improvements in bioavailability. The undesirable recrystallization rather reduces the bioavailability of the API. Poor bioavailability is a significant problem encountered in the development of pharmaceutical compositions, particularly those containing an API that is not highly water-soluble.

The influence on the supersaturation of low soluble compounds has been described by Gift et al., Influence of polymeric excipients on crystal hydrate formation kinetics in aqueous slurries. J Pharm Sci. 2008; 97(12):5198-211. Polyvinyl alcohol was successfully evaluated to inhibit the crystal formation of model compounds like caffeine. The grade of PVA used for these data is described as poly(vinyl alcohol) (PVA) with an average molecular weight of 47,000. No further specification or evaluation concerning the hydrolysis degree was given.

Another study using PVA to increase the supersaturated state of a model compound tacrolimus is described by Overhoff et al., Effect of Stabilizer on the Maximum Degree and Extent of Supersaturation and Oral Absorption of Tacrolimus Made By Ultra-Rapid Freezing. Pharmaceutical Research. 2008; 25(1):167-75. Solid dispersions are prepared by ultra rapid freeze drying. The used PVA grade is described as Poly(vinyl) alcohol (PVA, Mw 13,000-23,000, 87-89% hydrolyzed). PVA could be successfully used as a stabilizer.

The use of polyvinyl alcohol for hot melt extrusion has previously been described by de Jaeghere et al., Hot-melt extrusion of polyvinyl alcohol for oral immediate release applications. Int J Pharm. 2015; 492(1-2):1-9. Partly hydrolyzed PVA grades were used to evaluate the use as a carrier for oral immediate release dosage forms. An impact on release rates was observed, but no direct link between hydrolysis degree and supersaturation potential was identified.

Brough et al., Use of Polyvinyl Alcohol as a Solubility Enhancing Polymer for Poorly Water-Soluble Drug Delivery (Part 1), AAPS PharmSciTech Vol. 17, No. 1, p. 176 (Jan. 2, 2016) investigated certain PVA grades including PVA 4-75, PVA 4-88, PVA 4-98, PVA 4-38 by a non-sink gastric transfer dissolution method. It was apparent that after a pH-shift from 1.2 to 6.8 the solubility of the weakly basic model API itraconazole was rapidly decreasing. The 4-88 grade of PVA was determined to be effective at enhancing solubility and bioavailabilty of the model API itraconazole.

There is still a need for excipients having improved solubilization properties particularly after a pH change from acidic media to more neutral media.

SUMMARY OF THE INVENTION

It was surprisingly found that in a pharmaceutical composition comprising an amorphous solid dispersion of an API in a polymer matrix, a polyvinyl alcohol having a hydrolysis degree of 72% to 85%, and a viscosity of a 4% solution at 20° C. of 2 mPas to 4 mPas is particularly suitable as polymer for improving the supersaturation properties after dissolution of a poorly water-soluble API.

Unexpectedly, it was shown that there is an optimum range of hydrolysis degree and viscosity which allows a better potential for supersaturation of a poorly water-soluble API in aqueous media compared to actual existing and commonly used PVA grades. The PVA grades within this optimum range exhibit very good supersaturation properties in acidic aqueous media particularly for weakly basic APIs. Surprisingly, the supersaturation properties are still remarkably increased after a shift to almost neutral aqueous media compared to standard PVA grades, such as PVAs having a hydrolysis degree outside the range of 72% to 85%, and a viscosity outside the range of 2 mPas to 4 mPas.

In a preferred embodiment of the invention, the PVA has a hydrolysis degree of 80 to 85%, and a viscosity of a 4% solution at 20° C. of 2 mPas to 4 mPas.

The most preferred PVAs according to the invention have a hydrolysis degree of 80 to 83%, and a viscosity of a 4% solution at 20° C. of 3 mPas, particularly PVA 3-80 and PVA 3-83.

In another preferred embodiment of the invention, the amorphous solid dispersion of the API is obtainable by combining the PVA, and optionally further pharmaceutically acceptable components thereby obtaining the polymer matrix, and mixing the polymer matrix and the API at a temperature above the glass transition temperature or melting temperature of the polymer matrix thereby forming an amorphous solid dispersion of the active pharmaceutical ingredient. Preferably, the temperature is at least the melting temperature of the API.

In another aspect, the invention provides an oral dosage form comprising the pharmaceutical composition according to the invention in form of tablets, beads, granules, pellets, capsules, suspensions, emulsions, gels, films.

A further aspect of the invention concerns a method for enhancing solubility of an API in aqueous media, the method comprising mixing at least one poorly soluble active pharmaceutical ingredient and a polyvinyl alcohol having a hydrolysis degree of 72% to 85%, and a viscosity of a 4% solution at 20° C. of 2 mPas to 4 mPas at a temperature above the glass transition temperature or melting temperature of the polymer matrix thereby forming an amorphous solid dispersion of the active pharmaceutical ingredient. Preferably the the solubility of the active pharmaceutical ingredient in aqueous media is enhanced compared to the solubility of the active pharmaceutical in an amorphous solid dispersion containing a polyvinyl alcohol having a hydrolysis degree outside the range of 72% to 85% and/or a viscosity outside the range of 2 mPas to 4 mPas. The method can be applied in acidic conditions or gastric conditions having a pH of 1 to 2, particular 1 to 1.2. The method is particularly suitable for enhancing the solubility of an API in neutral media having a pH of 6 to 8, particularly a pH of 6.5 to 7.5.

DETAILED DESCRIPTION OF THE INVENTION

The present invention discloses a pharmaceutical composition comprising an amorphous solid dispersion of at least one active pharmaceutical ingredient in a polymer matrix wherein the active pharmaceutical ingredient is preferably poorly soluble, and wherein the polymer is polyvinyl alcohol having a hydrolysis degree of 72% to 85%, and a viscosity of a 4% solution at 20° C. of 2 mPas to 4 mPas.

The active pharmaceutical ingredients (API) of the pharmaceutical compositions according to the invention is dispersed in the polymer matrix. The API is a biologically active agent in form of a weak base, a weak acid or a neutral molecule. The API may be in the form of one or more pharmaceutically acceptable salts, esters, derivatives, analogues, prodrugs, and solvates thereof. The pharmaceutical composition may comprise more than one API.

As used herein, the terms "poorly soluble API", "poorly water-soluble API" and "lipophilic API" refer to an API having a solubility such that the highest therapeutic dose of the particular API to be administered to an individual cannot be dissolved in 250 ml of aqueous media ranging in pH from 1 to 8 following the definition of low solubility according to the Biopharmaceutics Classification System (BCS) classes 2 and 4. Poorly soluble APIs with weakly basic or weakly acidic characteristics have a pH-dependent solubility profile and can have a wide range of solubility in the aqueous environment of the gastrointestinal tract. APIs falling under BCS classes 2 or 4, respectively, are well known to persons skilled in the art.

As used herein, the term "weakly basic API" refers to a basic active pharmaceutical ingredient (API) wherein the basic API does not completely ionize in water.

According to an embodiment of the invention, the API included in the pharmaceutical compositions of the present invention has a sufficient amount to be therapeutically effective. For a given API, therapeutically effective amounts are generally known or readily accessible by persons skilled in the art. Typically, the API may be present in the pharmaceutical composition in a weight ratio of API to the polymeric matrix the range of 1:99 to (90:10), preferably 5:95 to 60:40, most preferably 10:90 to 30:70.

Polyvinyl alcohol (PVA) is a synthetic water-soluble polymer that has the idealized formula $[CH_2CH(OH)]_n$. It possesses good film-forming, adhesive, and emulsifying properties. PVA is prepared from polyvinyl acetate, where the functional acetate groups are either partially or completely hydrolysed to alcohol functional groups. If not completely hydrolysed, PVA is a random copolymer consisting of vinyl alcohol repeat units $—[CH_2CH(OH)]—$ and vinyl acetate repeat units $—[CH_2CH(OOCCH_3)]—$. The polarity of PVA is closely linked to its molecular structure. The hydrolysis degree and the molecular weight determine the molecular properties of PVA. As the degree of hydrolysis of acetate groups increases, the solubility of the polymer in aqueous media and also crystallinity and melting temperature of the polymer increase. However, at high hydrolysis degrees over 88%, the solubility of PVA decreases again. PVA is generally soluble in water, but almost insoluble in almost all organic solvents, excluding, in some cases, ethanol.

The typical PVA nomenclature indicates the viscosity of a 4% solution at 20° C. and the degree of hydrolysis of the polymer. For example, PVA 3-83 is a PVA grade with a viscosity of 3 mPas that is 83% hydrolysed, i.e. having 83% of vinyl alcohol repeat units and 17% of vinyl acetate repeat units. A skilled person is aware that a hydrolysis grade of 83% and a viscosity of 3 mPas encompasses calculated hydrolysis grades of 82.50% to 83.49% and calculated viscosities of 2.50 mPas to 3.49 mPas % according to common rounding methods. Viscosity according to the invention is measured as stated in USP 39 under Monograph "Polyvinyl Alcohol" with the method Viscosity-Rotational Method (912).

The degree of hydrolysis according to the invention is measured by determining the saponification value of the Polyvinyl Alcohol, e.g. as stated in USP 39 under Monograph "Polyvinyl Alcohol" under "Degree of Hydrolysis":

Sample: 1 g of Polyvinyl Alcohol, previously dried at 110° to constant weight

Analysis:

Transfer the Sample to a wide-mouth, 250-ml conical flask fitted by means of a suitable glass joint to a reflux condenser. Add 35 ml of dilute methanol (3 in 5), and mix gently to ensure complete wetting of the solid. Add 3 drops of phenolphthalein TS, and add 0.2 N hydrochloric acid or 0.2 N sodium hydroxide if necessary, to neutralize. Add 25.0 ml of 0.2 N sodium hydroxide VS, and reflux gently on a hot plate for 1 h. Wash the condenser with 10 ml of water, collecting the washings in the flask, cool, and titrate with 0.2 N hydrochloric acid VS. Concomitantly perform a blank determination in the same manner, using the same quantity of 0.2 N sodium hydroxide VS.

Calculation of Saponification Value:

Calculate the saponification value:

$$Result=[(V_B-V_B)\times N\times M_r]/W$$

$V_B$=volume of 0.2 N hydrochloric acid VS consumed in the titration of the blank (ml)

$V_S$=volume of 0.2 N hydrochloric acid VS consumed in the titration of the Sample solution (ml)

N=actual normality of hydrochloric acid VS $M_r$=molecular weight of potassium hydroxide, 56.11

W=weight of the portion of Polyvinyl Alcohol taken (g)

Calculation of Degree of Hydrolysis:

Calculate the degree of hydrolysis, expressed as a percentage of hydrolysis of polyvinyl acetate:

$$Result=100-[7.84\times S/(100-0.075\times S))$$

S=saponification value of the Polyvinyl Alcohol

According to the present invention, it was surprisingly found that PVAs having a degree of hydrolysis in the range of 72% to 85%, and a viscosity of a 4% solution at 20° C. of 2 mPas to 4 mPas show a superior performance in providing a prolongation of the supersaturated state of a poorly soluble API. Experiments unexpectedly showed that PVA having a hydrolysis degree higher than 85% or lower than 78% and a viscosity of a 4% solution at 20° C. of higher than 4 mPas do not exhibit a comparable performance in supersaturation of model APIs particularly under nearly neutral pH conditions at pH 6.8.

It is assumed that by varying the PVA hydrolysis grade, PVAs having an adjustable ratio of hydrogen bond donating hydroxyl groups are provided which may function as a solubility enhancer for poorly soluble APIs and particularly for poorly soluble APIs which are weakly basic independently of environmental pH conditions.

Preferred PVAs have a hydrolysis degree of 80% to 85%, and a viscosity of a 4 solution at 20° C. of 2 mPas to 4 mPas. Particularly preferred PVAs have a hydrolysis degree of 80% to 83%, and a viscosity of a 4% solution at 20° C. of 3 m Pas. The most preferred PVAs are PVA 3-80 and PVA 3-83.

It was found that PVAs having the above-identified viscosity and hydrolysis grades assure and stabilize the release and supersaturation of the poorly soluble API in aqueous media thereby preventing crystallization and phase separation. Since a low water solubility of an API in general accompanies a low bioavailability after its administration in a pharmaceutical preparation, the compositions according to the invention also contribute to improving the bioavailability of poorly water-soluble APIs, and particularly weakly basic APIs. Surprisingly, the enhanced supersaturation of the API was also pronounced in nearly neutral aqueous media reflecting the more neutral environment in the intestine.

As used herein, "bioavailability" is a term meaning the degree to which an API becomes available to the target tissue after being administered to the body of a patient.

The use of PVA grades according to the invention in a polymer matrix for pharmaceutical compositions is of interest for the formulation of solid oral pharmaceutical dosage forms with an instant, immediate or prolonged API release.

In a preferred embodiment of the invention, the polymer matrix may be combined with other pharmaceutically acceptable excipients. Particularly, the pharmaceutical composition according to the invention may comprise additional pharmaceutically acceptable hydrophilic or lipophilic polymers. The pharmaceutical composition may also comprise flow control agents, such as silicon dioxide, fillers, plasticizers, surfactants, and other suitable components that are well known to those skilled in the art. For the avoidance of doubt, other suitable components, e.g. flow control agents, such as silicon dioxide, are not needed for the beneficial properties according to the invention, e.g. improving the bioavailability of poorly water-soluble APIs, and particularly weakly basic API. Yet those components can be used for other purposes, e.g. to optimize the process of manufacturing of the pharmaceutical composition or oral dosage form according to the invention.

As used herein, the phrase "pharmaceutically acceptable" refers to all compounds, such as solvents, dispersion media, flow control agents, excipients, carriers, coatings, active agents, isotonic and absorption delaying agents, and the like that do not produce an allergic or similar untoward reaction when administered to humans in general. The use of such media and agents in pharmaceutical compositions is well known in the art.

As used herein, the term "amorphous solid dispersion" is a dispersion of an amorphous API in a polymer matrix. Preferably, the amorphous API is distributed in a molecularly dispersed state within the polymer matrix. In this case, the solid dispersion is a solid solution. Upon dissolution, formulations comprising an amorphous solid dispersion can reach higher solubilities in aqueous media than the crystalline API.

According to an embodiment of the invention, preferred methods for preparing the pharmaceutical composition include, but are not limited to hot-melt extrusion, injection molding, compression molding and additive manufacturing with hot-melt extrusion being the most preferred method.

According to a preferred embodiment of the invention, the amorphous solid dispersion is obtainable by mixing the at least one active pharmaceutical ingredient, the polyvinyl alcohol and optionally further pharmaceutically acceptable components at a temperature above the glass transition temperature or melting temperature of the polymer matrix thereby forming an amorphous solid dispersion of the active pharmaceutical ingredient. Preferably, the temperature is at least the melting temperature of the API in order to facilitate a uniform distribution of the amorphous API throughout the polymer matrix.

According to the invention, the minimum working temperature for obtaining an amorphous solid dispersion of the API is the temperature above which the PVA is in a molten state, i.e. generally a temperature above the glass transition temperature or melting temperatures of the PVA. For facilitating the formation of a uniform distribution of the API, preferably in amorphous form, in the polymer matrix, the working temperature is preferably at least the melting temperature of the API. In case the API solubilizes in the molten polymer matrix, working temperature can also be below the melting temperature of the API.

Pharmaceutical compositions according to the invention may be included in oral dosage forms in form of tablets, beads, granules, pellets, capsules, suspensions, emulsions, gels, or films.

Having entered the gastrointestinal tract, the polymer matrix of the oral dosage form swells and disintegrates in the aqueous environment of the gastrointestinal fluids thereby releasing the API. While a salt form of a weakly basic API may show improved initial aqueous concentration in the acidic gastric fluid, the weakly basic API rapidly converts to the free base form in the more neutral intestinal fluid where the free base-form of the API has a significantly lower equilibrium concentration. It was shown that PVAs included in dosage forms according to the invention maintain enhanced concentrations of the API in model solutions simulating acidic and neutral gastrointestinal solutions as compared to commonly used PVAs. Therefore, the pharmaceutical compositions according to the invention have shown to have the potential to provide enhanced bioavailability of poor solubility APIs when administered in oral dosage forms. The solubility-improved form of the API in the presence of a PVA grade according to the invention provides a concentration of the API in gastric fluid or simulated gastric fluid that is greater than the concentration of the API provided in the presence of commonly used PVA grades.

A further embodiment of the invention is a method for enhancing solubility of an active pharmaceutical ingredient in aqueous media, the method comprising mixing at least one poorly soluble active pharmaceutical ingredient and a polyvinyl alcohol having a hydrolysis degree of 72% to 85%, and a viscosity of a 4% solution at 20° C. of 2 mPas to 4 mPas at a temperature above the glass transition temperature or melting temperature of the polymer matrix thereby forming an amorphous solid dispersion of the active pharmaceutical ingredient.

According to a preferred embodiment of the invention, the solubility of the active pharmaceutical ingredient in aqueous media is enhanced compared to the solubility of the active pharmaceutical in an amorphous solid dispersion containing a polyvinyl alcohol having a hydrolysis degree outside the range of 72% to 85% and/or a viscosity outside the range of 2 mPas to 4 mPas.

The enhancement of the solubility of the active pharmaceutical ingredient in aqueous media can preferably be seen in acidic and neutral pH. Acidic pH according to the invention is a pH range below pH 7, particular a pH of 1 to 2, more particular a pH of 1 to 1.2. More preferably the solubility is enhanced at a neutral pH. Neutral pH according to the invention is a pH range of 6 to 8, more preferably at a pH of 6.5 to 7.5.

Having entered the gastrointestinal tract, the pharmaceutical composition for oral administration comprising an amorphous solid dispersion is first exposed to gastric acid followed by more neutral fluids in the intestinal tract. Solubility of the amorphous solid dispersion is additionally enhanced after such a pH-shift in the aqueous media from a pH between 1 to 2 to a pH between 6 to 8, preferably from a pH between 1 to 1.2 to a pH between 6.5 to 7.5.

In the context of the invention, enhancement of solubility also covers the effects of a prolonged solubilty, an enhanced and/or prolonged supersaturation and a reduced precipitation of the active pharmaceutical ingredient, preferably after the pH shift from an acidic to a neutral medium. These effects can be seen in the dissolution experiment, e.g. FIGS. 2 and 4. According to the invention, these effects can be used interchangeably.

Therefore, an embodiment of the invention is a process of enhancing solubility of an active pharmaceutical ingredient in aqueous media using a pharmaceutical composition comprising an amorphous solid dispersion of at least one active pharmaceutical ingredient in a polymer matrix, wherein the polymer is polyvinyl alcohol having a hydrolysis degree of 72% to 85%, and a viscosity of a 4% solution at 20° C. of 2 m Pas to 4 m Pas.

Preferably the aqueous medium has a pH of 6 to 8.

In a preferred embodiment, the solubilty is enhanced after a pH shift from a medium with an acidic pH to a medium with a neutral pH. More preferably, the medium with an acidic pH has a pH between 1 to 2 and the medium with a neutral pH has a pH between 6 to 8.

A further embodiment of the invention is a process as mentioned above, wherein the polyvinyl alcohol has a hydrolysis degree of 80% to 85%, and a viscosity of a 4% solution at 20° C. of 2 mPas to 4 mPas. Preferably, the polyvinyl alcohol has a hydrolysis degree of 80% to 83%, and a viscosity of a 4% solution at 20° C. of 3 mPas. More preferably, the polyvinyl alcohol is PVA 3-80, PVA 3-82 or PVA 3-83.

In a further embodiment of the invention, the active pharmaceutical ingredient is poorly soluble.

A further embodiment of the invention is a process according to any one of claims 1 to 8, wherein the amorphous solid dispersion is obtainable by mixing the at least one active pharmaceutical ingredient, the polyvinyl alcohol and optionally further pharmaceutically acceptable components at a temperature above the glass transition temperature or melting temperature of the polymer matrix thereby forming an amorphous solid dispersion of the active pharmaceutical ingredient. Preferably, the temperature is at least the melting temperature of the active pharmaceutical ingredient.

A further embodiment of the invention is a pharmaceutical composition obtainable by the process as mentioned above.

A further embodiment of the invention is an oral dosage form comprising a pharmaceutical composition as mentioned above in form of tablets, beads, granules, pellets, capsules, suspensions, emulsions, gels, films.

A further embodiment of the invention is a process of preparing a pharmaceutical composition as mentioned above, comprising the steps of mixing a poorly soluble active pharmaceutical ingredient and a polyvinyl alcohol having a hydrolysis degree of 72% to 85%, and a viscosity of a 4% solution at 20° C. of 2 mPas to 4 mPas, and optionally further pharmaceutically acceptable components at a temperature above the glass transition temperature or melting temperature of the polymer matrix, thereby forming an amorphous solid dispersion of the active pharmaceutical ingredient. Preferably, the polyvinyl alcohol has a hydrolysis degree of 80% to 83%, and a viscosity of a 4% solution at 20° C. of 3 mPas. More preferably, the temperature is at least the melting temperature of the active pharmaceutical ingredient.

In a preferred embodiment of the invention, the method for enhancing solubility of an active pharmaceutical ingredient in aqueous media comprises a polyvinyl alcohol having a hydrolysis degree of 80% to 85%, and a viscosity of a 4% solution at 20° C. of 2 mPas to 4 mPas. More preferably, the polyvinyl alcohol has a hydrolysis degree of 80% to 83%, and a viscosity of a 4% solution at 20° C. of 3 mPas. Most preferably the PVA is PVA 3-80 or PVA 3-83.

A further embodiment of the invention is a process of preparing a pharmaceutical composition as described above, comprising the steps of mixing a poorly soluble active pharmaceutical ingredient and a polyvinyl alcohol having a hydrolysis degree of 72% to 85%, and a viscosity of a 4% solution at 20° C. of 2 mPas to 4 mPas, and optionally further pharmaceutically acceptable components at a temperature above the glass transition temperature or melting temperature of the polymer matrix, thereby forming an amorphous solid dispersion of the active pharmaceutical ingredient. Preferably the temperature is at least the melting temperature of the active pharmaceutical ingredient.

BRIEF DESCRIPTION OF THE FIGURES

FIG. 1 shows a table summarizing extrusion parameters for preparing model extruded matrix systems with varying PVA grades and itraconazole (ITZ) as a lipophilic model API.

FIG. 3 shows a table summarizing extrusion parameters for preparing model extruded matrix systems with varying PVA grades and dipyridamole as a lipophilic model API.

EXAMPLES

Figure 2:
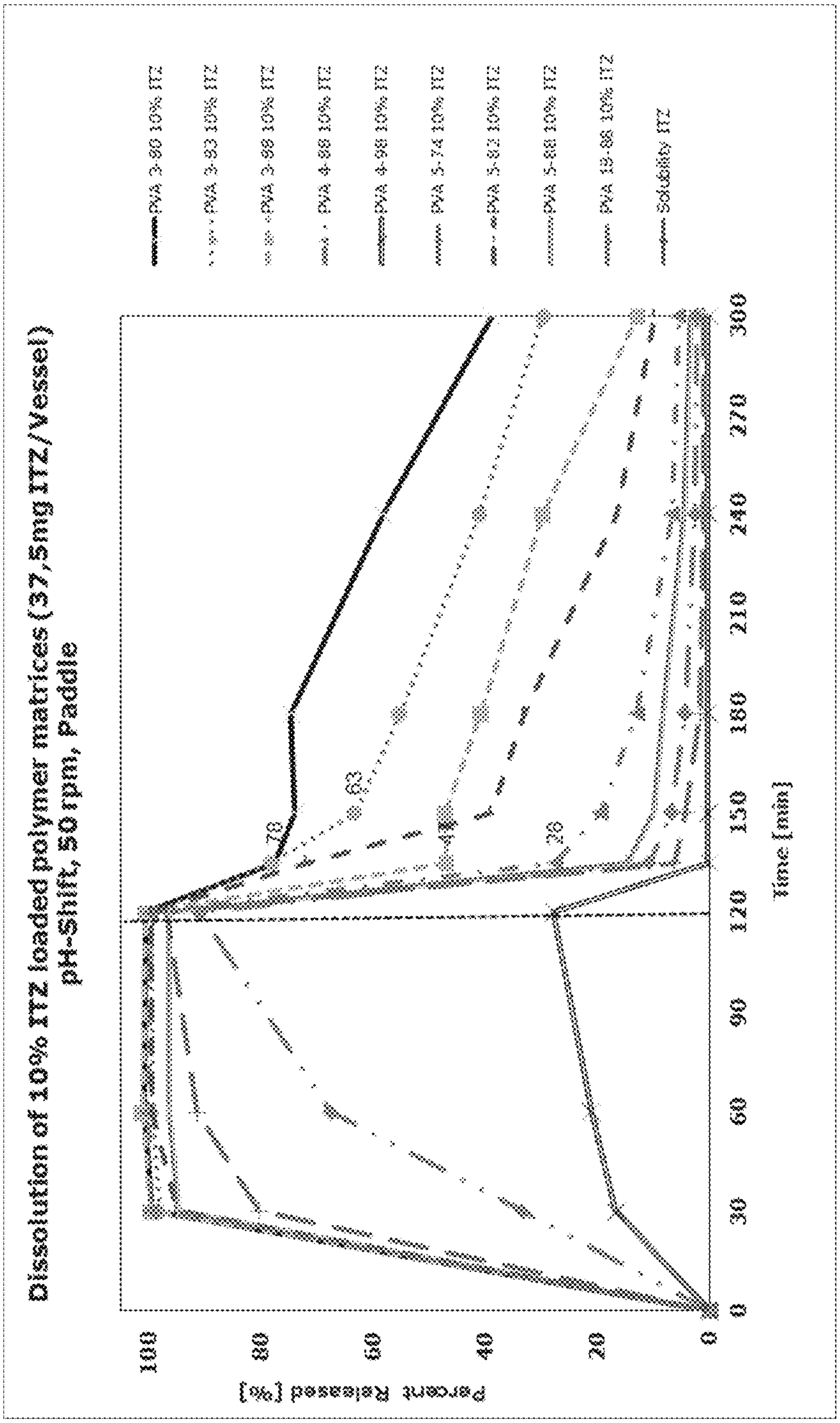
FIG. 2 shows dissolution profiles of extruded matrices comprising different PVA grades and itraconazole (ITZ).

Example 1: Preparation of ITZ Loaded PVA Matrices

Nine samples of PVA matrices comprising 88% by weight PVA having varying PVA grades, 2% by weight silicon dioxide and 10% by weight itraconazole (ITZ) (BCS class 2) were prepared by hot melt extrusion as follows:

One of the PVA grades PVA 5-74, PVA 3-80, PVA 5-82, PVA 3-83, PVA 5-88, PVA 3-88, PVA 4-88 (Parteck MXP), PVA 4-98, and PVA 18-88, respectively, was used for preparing the ITZ loaded PVA matrices.

The respective PVA was dried in a vacuum drying oven for 1 hour at 85° C. and 100 mbar vacuum in a porcelain dish. The PVA was then briefly allowed to cool. The PVA, ITZ and silicon dioxide were weighed into a 1 L mixing vessel according to the weight ratios shown in FIG. 1 and then mixed by means of a tubular mixer for 5 minutes. Silicon dioxide was added as a flow control agent to the powder mixtures since the model API itraconazole is poorly flowable. The powder mixture was then filled into the gravimetric twin-screw feeder of a Brabender KETSE 12/36 extruder and a determination of the maximum feed rate was performed.

The heating zones were heated until the respective target temperatures as shown in FIG. 1 were reached.

After the heating zones had reached their respective temperatures, the speed and, analogously, the dosing rate of the powder mixture was increased step by step in units of 50 until the target speed and target dosing rate of 200 rpm and 200.0 g/h, respectively, were reached. The extrudate was discarded for about 5 minutes until nozzle pressure and torque stabilized. The extrudate was then allowed to cool on the conveyor belt at room temperature and thereby conveyed to the pelletizer, where the extrudate was crushed into 1.5 mm pellets using a Brabender pelletizer. The process was continued until the powder mixture in the feeder was used up. This was reflected in incipient fluctuations in the dosing rate.

The so obtained extruded samples were used for dissolution experiments.

Example 2: Dissolution Profiles of 10% ITZ Loaded PVA Matrices

The dissolution behavior of the extrudates was evaluated in accordance with a pH shift method originally described in the Pharmacopoea Europaea 9.0 for testing gastric juice resistance of oral formulations.

Sample Preparation:

The extrudates were ground in an IKA Tubemill 100 with a 40 ml disposable grinding cup for 20 sec at 25000 rpm. 3 samples of each extrudate were prepared. For each sample, 375 mg of extrudate were weighed corresponding to 37.5 mg ITZ per sample.

Dissolution Method:

The dissolution rates of ITZ from the extrudates were measured using a Sotax AT7 smart measuring system equipped with a fraction collector and a buffer station. The samples were placed in dissolution vessels containing 750 mL 0.1 M HCl with a paddle rotation of 50 rpm. After 120 min, 250 ml of preheated (37° C.±0.5) 0.2 M Na3PO4×12 $H_2O$ were added via the buffer station to a total volume of 1000 mL. 2.5 mL samples were taken at 30, 60, 120 min and after the pH shift to pH 6.8, at 135, 150, 180, 240 and 300 min.

HPLC Conditions:

The so obtained dissolution samples were analyzed with an Agilent 1260 Infinity or 1260 Infinity II system equipped with a Chromolith® Performance RP-18e 100-4.6 mm column (Merck) and UV detection. The HPLC system was operated under isocratic conditions with Mobile Phase Itraconazole (450/450/200 tetrabutylammonium hydrogen sulfate (TBAHS) of Molecula 1.7 g/1000 mL, acetonitrile Merck LiChrosolv® Reag. Ph Eur for HPLC, and methanol LiChrosolv® Reag. Ph Eur for HPLC.

The dissolution samples were filtered, directly diluted 1:1 with Mobile Phase Itraconzole, mixed and analyzed by HPLC with the following parameters:

Runtime: 7 min
Flow: 2.1 ml
Detection wavelength: 254 nm
Injection volume: 15 μl
Column oven temperature: 30° C.
Retention Time Peak: 4 min The results are shown in FIG. 2. It was found that the weakly basic API ITZ showed very good solubility in the presence of PVA 3-80, PVA 3-83, PVA 3-88, PVA 5-82, and PVA 4-88 in acidic solution. However, after the pH-shift to neutral conditions at 120 min, PVA 3-80 and PVA 3-83 showed an outstanding performance in maintaining the release of the free base form ITZ at a sufficient level as compared to PVA 4-88, PVA 5-88, PVA 18-88, PVA 5-74 and PVA 4-98. PVA 3-88 and PVA 5-82 only showed a moderate performance.

Example 3: Preparation of Dipyridamole Loaded PVA Matrices

Four samples of PVA matrices comprising 90% by weight PVA having varying PVA grades, and 10% by weight dipyridamole (BCS class 2) were prepared by hot melt extrusion as follows:

One of the PVA grades PVA 3-80 (Poval 3-80, Kuraray Europe GmbH), PVA 3-83 (Poval 3-83, Kuraray Europe GmbH), and PVA 4-88 (Parteck MXP, Merck KGaA), respectively, was used for preparing the dipyridamole loaded PVA matrices The respective PVA sample was dried in a vacuum drying oven for 1 hour at 85° C. and 100 mbar vacuum in a porcelain dish. The PVA was then briefly allowed to cool. The PVA and dipyridamole were weighed into a 1 L mixing vessel according to the weight ratios shown in FIG. 3 and then mixed by means of a tubular mixer for 5 minutes. The powder mixture was then filled into the gravimetric twin-screw feeder of a Thermo-Fisher Pharma 11 extruder and a determination of the maximum feed rate was performed.

The heating zones were heated until the respective target temperatures as shown in FIG. 1 were reached.

After the heating zones had reached their respective temperatures, the speed and, analogously, the dosing rate of the powder mixture was increased step by step in units of 50 until the target speed and target dosing rate of 200 rpm and 200.0 g/h, respectively, were reached. The extrudate was discarded for about 5 minutes until nozzle pressure and torque stabilized. The extrudate was then allowed to cool on the conveyor belt at room temperature and thereby conveyed to the pelletizer, where the extrudate was crushed into 1.5 mm pellets using a Brabender pelletizer. The process was continued until the powder mixture in the feeder was used up. This was reflected in incipient fluctuations in the dosing rate.

The so obtained extruded samples were used for dissolution experiments.

Example 4: Dissolution Profiles of 10% Dipyridamole Loaded PVA Matrices

The dissolution behavior of the extrudates was evaluated in accordance with a pH shift method originally described in the Pharmacopoea Europaea 9.0 for testing gastric juice resistance of oral formulations.

Sample Preparation:

The extrudates were ground in an IKA Tubemill 100 with a 40 ml disposable grinding cup for 20 sec at 25000 rpm. 3 samples of each extrudate were prepared. For each sample, 500 mg of extrudate were weighed corresponding to 50 mg dipyridamole per sample.

Dissolution Method:

The dissolution rates of ITZ from the extrudates were measured using a Sotax AT7 smart measuring system equipped with a fraction collector and a buffer station. The samples were placed in dissolution vessels containing 750 mL 0.1 M HCl with a paddle rotation of 50 rpm. After 120 min, 250 ml of preheated (37° C.±0.5) 0.2 M Na3PO4×12 H2O were added via the buffer station to a total volume of 1000 mL. 2.5 mL samples were taken at 30, 60, 120 min and after the pH shift to pH 6.8, at 135, 150, 180, 240 and 300 min.

HPLC Conditions:

The so obtained dissolution samples were analyzed with an Agilent 1260 Infinity or 1260 Infinity II system equipped with a Chromolith® Performance RP-18e 100-4.6 mm column (Merck) and UV detection. The HPLC system was operated under isocratic conditions with Mobile Phase Dipyridamole (450/450/200 tetrabutylammonium hydrogen sulfate (TBAHS) of Molecula 1.7 g/1000 mL, acetonitrile Merck LiChrosolv® Reag. Ph Eur for HPLC, and methanol LiChrosolv® Reag. Ph Eur for HPLC).

Figure 4:
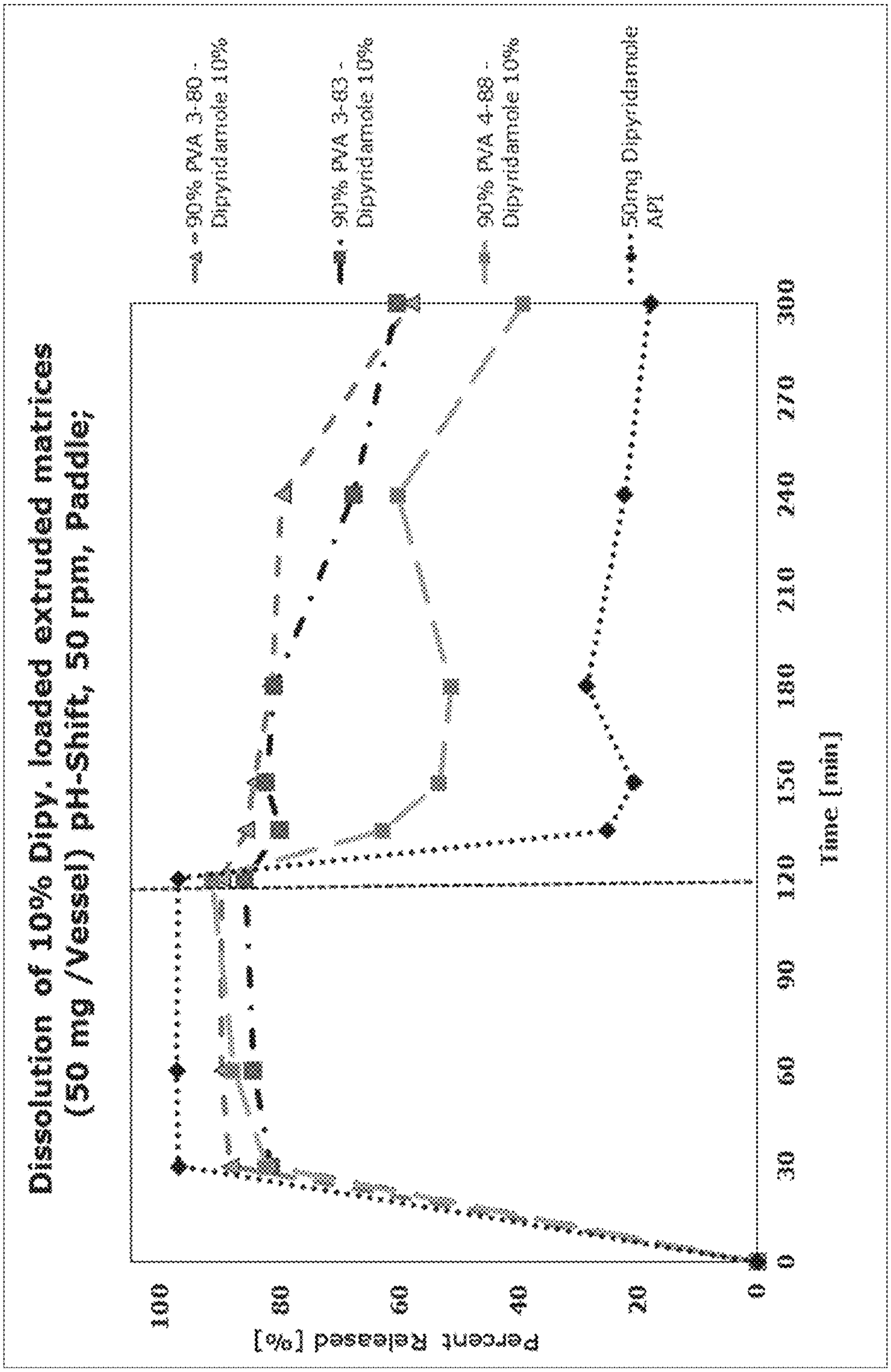
FIG. 4 shows dissolution profiles of extruded matrices comprising different PVA grades and dipyridamole.

The dissolution samples were filtered, directly diluted 1:1 with Mobile Phase Dipyridamole, mixed and analyzed by HPLC with the following parameters:

Runtime: 7 min
Flow: 2.1 ml
Detection wavelength: 254 nm
Injection volume: 15 μl
Column oven temperature: 30° C.
Retention Time Peak: 3.0 min The results are shown in FIG. 4. It was found that the weakly basic API dipyridamole showed very good solubility in the presence of PVA 3-80, PVA 3-83, and PVA 4-88 in acidic solution with PVA 4-88 showing the most rapid and almost complete release of the dipyridamole. After the pH-shift to neutral conditions at 120 min, PVA 3-80 and PVA 3-83 showed a very good performance in maintaining the release of the free base form of dipyridamole at a high level as compared to PVA 4-88.

The invention claimed is:

1. A pharmaceutical composition comprising:

an amorphous solid dispersion of at least one weakly basic active pharmaceutical ingredient in a polymer matrix, wherein the polymer is polyvinyl alcohol having a hydrolysis degree of 80%-83%, and a viscosity of a 4% solution at 20° C. of 3 mPas.

2. The pharmaceutical composition according to claim 1, wherein the amorphous solid dispersion has a greater solubility than the weakly basic active pharmaceutical ingredient alone.

3. The pharmaceutical composition according to claim 2, wherein the pharmaceutical composition has a pH between 6 to 8.

4. The pharmaceutical composition according to claim 1, wherein the polyvinyl alcohol is PVA 3-80, PVA 3-82 or PVA 3-83.

5. The pharmaceutical composition according to claim 1, wherein the active pharmaceutical ingredient is poorly soluble.

6. The pharmaceutical composition according to claim 1 in form of tablets, beads, granules, pellets, capsules, suspensions, emulsions, gels, films.

7. A process of preparing a pharmaceutical composition according to claim 1, comprising:

forming an amorphous solid dispersion of the active pharmaceutical ingredient by mixing a poorly soluble active pharmaceutical ingredient and a polyvinyl alcohol having a hydrolysis degree of 80% to 83%, and a viscosity of a 4% solution at 20° C. of 3 mPas at a temperature above the glass transition temperature or melting temperature of the polymer matrix.

8. The process according to claim 7, wherein the temperature is at least the melting temperature of the active pharmaceutical ingredient.

9. The process of preparing a pharmaceutical composition of claim 7 additionally comprising mixing at least one additional pharmaceutically acceptable component when forming the amorphous solid dispersion.

* * * * *